(12) United States Patent
Oliver et al.

(10) Patent No.: US 7,993,675 B2
(45) Date of Patent: *Aug. 9, 2011

(54) SOLVATING SYSTEM AND SEALANT FOR MEDICAL USE IN THE SINUSES AND NASAL PASSAGES

(75) Inventors: Dana A. Oliver, Jacksonville, FL (US); Cecil O. Lewis, Jacksonville, FL (US); Edze Jan Tijsma, Maastricht (NL); Maria Nieves Gonzalez Lopez, Maastricht (NL); Matthew F. Myntti, St. Augustine, FL (US); James Britton Hissong, Jacksonville, FL (US)

(73) Assignee: Medtronic Xomed, Inc., Jacksonville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 11/739,480

(22) Filed: Apr. 24, 2007

(65) Prior Publication Data

US 2007/0264342 A1 Nov. 15, 2007

Related U.S. Application Data

(63) Continuation-in-part of application No. 11/431,495, filed on May 10, 2006.

(51) Int. Cl.
*A61K 9/00* (2006.01)

(52) U.S. Cl. .................................................. 424/486

(58) Field of Classification Search ................ None
See application file for complete search history.

(56) References Cited

U.S. PATENT DOCUMENTS

| | | | |
|---|---|---|---|
| 3,422,186 A | 1/1969 | Sasmor | |
| 4,002,775 A | 1/1977 | Kabara | |
| 4,107,328 A | 8/1978 | Michaels | |
| 4,851,521 A | 7/1989 | Della Valle et al. | |
| 5,017,229 A | 5/1991 | Burns et al. | |
| 5,166,331 A | 11/1992 | Della Valle et al. | |
| 5,208,257 A | 5/1993 | Kabara | |
| 5,229,103 A | 7/1993 | Eagle et al. | |
| 5,246,964 A | 9/1993 | Ueno | |
| 5,290,552 A | 3/1994 | Sierra et al. | |
| 5,326,567 A | 7/1994 | Capelli | |
| 5,336,163 A | 8/1994 | DeMane et al. | |
| 5,442,053 A | 8/1995 | Della Valle et al. | |
| 5,480,658 A | 1/1996 | Melman | |
| 5,575,815 A * | 11/1996 | Slepian et al. | 600/36 |
| 5,601,594 A | 2/1997 | Best | |
| 5,631,241 A | 5/1997 | Della Valle et al. | |
| 5,644,049 A | 7/1997 | Giusti et al. | |
| 5,662,913 A | 9/1997 | Capelli | |
| 5,676,964 A | 10/1997 | Della Valle et al. | |
| 5,693,065 A | 12/1997 | Rains, III | |
| 5,709,546 A | 1/1998 | Waggoner | |
| 5,716,981 A | 2/1998 | Hunter et al. | |
| 5,739,176 A | 4/1998 | Dunn et al. | |
| 5,763,410 A | 6/1998 | Edwardson et al. | |
| 5,895,781 A | 4/1999 | Neumiller et al. | |
| 5,925,334 A | 7/1999 | Rubin et al. | |
| 5,968,542 A | 10/1999 | Tipton | |
| 6,001,870 A | 12/1999 | Henkel | |
| 6,013,657 A | 1/2000 | Lavon et al. | |
| 6,063,061 A | 5/2000 | Wallace et al. | |
| 6,071,305 A | 6/2000 | Brown et al. | |
| 6,129,761 A | 10/2000 | Hubbell | |
| 6,143,330 A | 11/2000 | Aaltonen et al. | |
| 6,156,294 A | 12/2000 | Mautone | |
| 6,156,792 A | 12/2000 | Hatton et al. | |
| 6,203,822 B1 | 3/2001 | Schlesinger et al. | |
| 6,224,857 B1 | 5/2001 | Romeo et al. | |
| 6,248,371 B1 | 6/2001 | Domenico | |
| 6,284,804 B1 | 9/2001 | Singh et al. | |
| 6,342,251 B1 | 1/2002 | Illum et al. | |
| 6,372,229 B1 | 4/2002 | Ollerenshaw et al. | |
| 6,375,963 B1 | 4/2002 | Repka et al. | |
| 6,395,295 B1 | 5/2002 | Hills et al. | |
| 6,395,746 B1 | 5/2002 | Cagle et al. | |
| 6,423,333 B1 | 7/2002 | Stedronsky et al. | |
| 6,423,694 B1 | 7/2002 | Drutz et al. | |
| 6,541,116 B2 | 4/2003 | Michal et al. | |
| 6,541,460 B2 | 4/2003 | Petito | |
| 6,610,314 B2 | 8/2003 | Koenig et al. | |
| 6,613,084 B2 | 9/2003 | Yang | |
| 6,616,913 B1 | 9/2003 | Mautone | |
| 6,623,513 B2 | 9/2003 | Biel | |
| 6,623,521 B2 | 9/2003 | Steinke et al. | |
| 6,632,457 B1 | 10/2003 | Sawhney | |
| 6,676,930 B2 | 1/2004 | Mautone | |
| 6,685,697 B1 | 2/2004 | Arenberg et al. | |
| 6,686,346 B2 | 2/2004 | Nilsson et al. | |
| 6,706,290 B1 | 3/2004 | Kajander et al. | |
| 6,723,709 B1 | 4/2004 | Pressato et al. | |
| 6,762,160 B2 | 7/2004 | Barbeau et al. | |
| 6,770,729 B2 | 8/2004 | Van Antwerp | |
| 6,812,196 B2 | 11/2004 | Rees et al. | |
| 6,855,678 B2 | 2/2005 | Whiteley | |
| 6,867,233 B2 | 3/2005 | Roselle et al. | |
| 6,869,938 B1 | 3/2005 | Schwartz et al. | |
| 6,891,037 B1 | 5/2005 | Hasler et al. | |

(Continued)

FOREIGN PATENT DOCUMENTS

EP 0 530 861 B1 3/1993

(Continued)

OTHER PUBLICATIONS

Chang, DM, "The binding of free calcium ions in aqueous solution using chelating agents, phosphates and poly(acrylic acid)," JAOCS, vol. 60, No. 3, (Mar. 1983).*

(Continued)

*Primary Examiner* — David J Blanchard
*Assistant Examiner* — Suzanne Ziska
(74) *Attorney, Agent, or Firm* — IPLM Group, P.A.

(57) ABSTRACT

Chronic rhinosinusitis and other bacterial sinus conditions may be treated by applying a solvating system containing a surfactant to a bacterial biofilm in a nasal or sinus cavity, disrupting the biofilm, and applying a protective layer of a polymeric film-forming medical sealant.

31 Claims, 2 Drawing Sheets

U.S. PATENT DOCUMENTS

| | | |
|---|---|---|
| 6,919,348 B2 | 7/2005 | Wei |
| 6,936,579 B2 | 8/2005 | Urban |
| 6,953,772 B2 | 10/2005 | Lopes |
| 6,962,813 B2 * | 11/2005 | Pier et al. ............ 435/326 |
| 6,989,195 B2 | 1/2006 | Anderson |
| 7,090,882 B2 | 8/2006 | Koeford et al. |
| 7,119,217 B2 | 10/2006 | Jiang et al. |
| 7,128,897 B2 | 10/2006 | Osbakken et al. |
| 7,220,431 B2 | 5/2007 | Sawchuk et al. |
| 7,238,363 B2 | 7/2007 | Mansouri et al. |
| 7,244,841 B2 | 7/2007 | Love et al. |
| 7,341,983 B2 | 3/2008 | Pedersen et al. |
| 7,410,480 B2 | 8/2008 | Muni et al. |
| 7,446,089 B2 | 11/2008 | Singh et al. |
| 7,494,963 B2 | 2/2009 | Ahmed et al. |
| 7,544,192 B2 | 6/2009 | Eaton et al. |
| 7,714,011 B2 | 5/2010 | Clarot et al. |
| 2001/0044651 A1 | 11/2001 | Steinke et al. |
| 2001/0051613 A1 | 12/2001 | Illum et al. |
| 2002/0022588 A1 | 2/2002 | Wilkie et al. |
| 2002/0029015 A1 | 3/2002 | Camenzind et al. |
| 2002/0055158 A1 | 5/2002 | Greene et al. |
| 2002/0062147 A1 | 5/2002 | Yang |
| 2002/0187918 A1 | 12/2002 | Urban |
| 2003/0009213 A1 | 1/2003 | Yang |
| 2003/0079758 A1 | 5/2003 | Siegel et al. |
| 2003/0133883 A1 | 7/2003 | Finnegan et al. |
| 2003/0139382 A1 | 7/2003 | Wall et al. |
| 2003/0157687 A1 | 8/2003 | Greene et al. |
| 2003/0199969 A1 | 10/2003 | Steinke et al. |
| 2003/0235602 A1 | 12/2003 | Schwartz |
| 2004/0101506 A1 | 5/2004 | Fust |
| 2004/0106987 A1 | 6/2004 | Palasis et al. |
| 2004/0110738 A1 | 6/2004 | Gillis et al. |
| 2004/0116958 A1 | 6/2004 | Gopferich et al. |
| 2004/0117006 A1 | 6/2004 | Lewis et al. |
| 2004/0143001 A1 | 7/2004 | Love et al. |
| 2004/0204399 A1 | 10/2004 | Osbakken et al. |
| 2004/0213758 A1 | 10/2004 | Sefton et al. |
| 2004/0214753 A1 | 10/2004 | Britten et al. |
| 2005/0003007 A1 | 1/2005 | Bolx et al. |
| 2005/0032668 A1 | 2/2005 | Pedersen et al. |
| 2005/0042240 A1 | 2/2005 | Utterberg et al. |
| 2005/0043706 A1 | 2/2005 | Eaton et al. |
| 2005/0064508 A1 | 3/2005 | Belcher et al. |
| 2005/0080396 A1 * | 4/2005 | Rontal ............ 604/500 |
| 2005/0106728 A1 | 5/2005 | Burgess et al. |
| 2005/0147679 A1 | 7/2005 | Petito et al. |
| 2005/0220895 A1 | 10/2005 | Bucalo et al. |
| 2005/0226937 A1 * | 10/2005 | O'Hagan et al. ............ 424/492 |
| 2005/0244339 A1 | 11/2005 | Jauering et al. |
| 2005/0282722 A1 | 12/2005 | McReynolds et al. |
| 2006/0003008 A1 | 1/2006 | Gibson et al. |
| 2006/0018945 A1 | 1/2006 | Britigan et al. |
| 2006/0035808 A1 | 2/2006 | Ahmed et al. |
| 2006/0045850 A1 | 3/2006 | Namburi et al. |
| 2006/0051385 A1 * | 3/2006 | Scholz ............ 424/405 |
| 2006/0106361 A1 | 5/2006 | Muni et al. |
| 2006/0205621 A1 | 9/2006 | Borazjani et al. |
| 2006/0210605 A1 | 9/2006 | Chang et al. |
| 2007/0207192 A1 * | 9/2007 | Holl et al. ............ 424/449 |
| 2007/0264310 A1 | 11/2007 | Hissong et al. |
| 2007/0264342 A1 | 11/2007 | Oliver et al. |
| 2007/0264353 A1 | 11/2007 | Myntti et al. |
| 2008/0010947 A1 | 1/2008 | Huang et al. |
| 2008/0248558 A1 * | 10/2008 | Deinhammer et al. ....... 435/264 |
| 2009/0005339 A1 * | 1/2009 | Scholz et al. ............ 514/53 |
| 2010/0240770 A1 | 9/2010 | Qi et al. |

FOREIGN PATENT DOCUMENTS

| | | | |
|---|---|---|---|
| EP | 1 374 856 A1 | 1/2004 | |
| FR | 2 710 529 A1 | 4/1995 | |
| JP | 52-007428 | 1/1977 | |
| RU | 222 8203 | 5/2004 | |
| SU | 1128917 A1 | 12/1984 | |
| SU | 1699430 A1 | 12/1991 | |
| WO | WO 94/05330 | 3/1994 | |
| WO | WO 95/03036 | 2/1995 | |
| WO | WO 97/38698 | 10/1997 | |
| WO | WO 98/09622 | * 3/1998 | |
| WO | WO 99/27905 A | 6/1999 | |
| WO | WO 00/21510 | 4/2000 | |
| WO | WO 00/56283 | 9/2000 | |
| WO | WO 03/061579 A2 | 7/2003 | |
| WO | WO 03/092745 A1 | 11/2003 | |
| WO | WO 2004/009143 A1 | 1/2004 | |
| WO | WO 2004/024187 A2 | 3/2004 | |
| WO | WO 2005/000029 A2 | 1/2005 | |
| WO | WO 2005/089670 A1 | 9/2005 | |
| WO | WO 2006/099386 A2 | 9/2006 | |
| WO | WO 2008/097317 A1 | 8/2008 | |

OTHER PUBLICATIONS

Chang (JAOCS. vol. 60, No. 3, Mar. 1983).*

Post, J.C., "Direct evidence of bacterial biofilms in otitis media", Laryngoscope 111(12):2083-94 (2001).

Ehrlich et al., "Mucosal Biofilm Formation on Middle-Ear Mucosa in the Chinchilla Model of Otitis Media", JAMA 287(13):1710-15 (2002).

Fergie, N. et al., "Is otitis media with effusion a biofilm infection?", Clin Otolaryngol Allied Sci. 29(1):38-46 (2004).

Ferguson B.J. and Stolz D.B., "Demonstration of biofilm in human bacterial chronic rhinosinusitis", Am J Rhinol 19:452-457, 2005.

Ramadan H.H., Sanclement J.A. and Thomas J.G., "Chronic rhinosinusitis and biofilms", Otolaryngol Head Neck Surg. 132:414-417, 2005.

Benninger M.S., Ferguson B.J., Hadley J.A., et al., "Adult chronic rhinosinusitis: Definitions, diagnosis, epidemiology, and pathophysiology", Otolaryngol Head Neck Surg 129 (3 suppl):S1-S32, 2003.

Nadel D.M., Lanza D.C., and Kennedy D.W., "Endoscopically guided cultures in chronic sinusitis", Am J Rhinol 12:233-241, 1998.

Stepanovic S, Vukovic D, Dakic I, et al., "A modified microtiter-plate test for quantification of staphylococcal biofilm formation", J Microbiol Methods 40:175-179, 2000.

Gotz F., "Staphylococcus and biofilms", Mol Microbiol 43:1367-1378, 2002.

Lethbridge-çejku M, Rose D, Vickerie J. Summary health statistics for US adults: National Health Interview Survey, 2004. National Center for Health Statistics. Vital Health Stat 2006;10 (228). Available: http://www.cdc.gov/nchs/fastats/sinuses.htm.

Rosiak, J.M. et al., "Radiation Formation of Hydrogels For Biomedical Purposes. Some Remarks And Comments", Radiat. Phys. Chem. vol. 46, No. 2, pp. 161-168, 1995.

Costerton J.W., Stewart P.S. and Greenberg E.P., "Bacterial biofilms: A common cause of persistent infections", Science 284:1318-1322, 1999.

Morris D.P. and Hagr A., "Biofilm: Why the sudden interest?" J Otolaryngol 34(suppl 2):S56-S5, 2005.

Hall-Stoodley L, Hu F.Z., Gieseke A, et al., "Direct detection of bacterial biofilms on the middle-ear mucosa of children with chronic otitis media." JAMA 296:202-211, 2006.

Sanderson A.R., Leid J.G., and Hunsaker D., "Bacterial biofilms on the sinus mucosa of human subjects with chronic rhinosinusitis", Laryngoscope 116:1121-1126 (2006).

Sanclement J.A., Webster P., Thomas J., and Ramadan H.H., "Bacterial biofilms in surgical specimens of patients with chronic rhinosinusitis", Laryngoscope 115:578-582, 2005.

Bendouah Z., Barbeau J., Hamad W.A., and Desrosiers M., "Biofilm formation by *Staphylococcus aureus* and *Pseudomonas aeruginosa* is associated with an unfavorable evolution after surgery for chronic sinusitis and nasal polyposis", Otolaryngol Head Neck Surg. 134:991-996, 2006.

Bhattacharyya N., and Kepnes L.J., "The microbiology of recurrent rhinosinusitis after endoscopic sinus surgery", Arch Otolaryngol Head Neck Surg. 125:1117-1120, 1999.

Cryer J., Schipor I., Perloff J.R., and Palmer J.N., "Evidence of bacterial biofilms in human chronic sinusitis", ORL J Otorhinolaryngol Relat Spec 66:155-158, 2004.

Meltzer E.O., Hamilos D.L., Hadley J.A., et al., "Rhinosinusitis: Establishing definitions for clinical research and patient care", J Allergy Clin Immunol 114(suppl):S155-S212, 2004.

Chiu A.G., and Kennedy D.W., "Surgical management of chronic rhinosinusitis and nasal polyposis: a review of the evidence", Curr Allergy Asthma Rep 4:486-489, 2004.

Bhattacharyya N., "Clinical outcomes after endoscopic sinus surgery", Curr Opin Allergy Clin Immunol 6:167-171, 2006.

Wormald P.J., Psaltis A., and Ha K., "A sheep model for the study of biofilms in sinusitis", In Programs and abstracts of the 52nd Annual Meeting of the American Rhinologic Society, Toronto, Ontario, Canada, Sep. 16, 2006.

Anglen J.O., Apostoles S., Christensen G., and Gainor B., "The efficacy of various irrigation solutions in removing slime-producing *Staphylococcus*", J Orthop Trauma 8:390-396, 1994.

Chole, Richard A. and Faddis, Brian T., Evidence for Microbial Biofilms in Cholesteatomas, Arch Otolaryngol Head and Neck Surg. 2002; 128: 1129-1133. Downloaded Apr. 17, 2007 from Medtronic Xomed at www.archoto.com.

Desrosiers M. Refractory chronic rhinosinusitis: pathophysiology and management of chronic rhinosinusitis persisting after endoscopic sinus surgery. Curr Allergy Asthma Rep 2004;4:200-7.

Smith TL, Batra PS, Seiden AM, Hannley M. Evidence supporting endoscopic sinus surgery in the management of adult chronic sinusitis: a systematic review. Am J Rhinol 2005;19:537-43.

Perloff JR, Palmer JN. Evidence of bacterial biofilms on frontal recess stents in patients with chronic rhinosinusitis. Am J Rhinol 2004;18:377-80.

Wright ED, Frenkiel S. Infectious adult rhinosinusitis: etiology, diagnosis, and management principles. J Otolaryngol 2005;34(suppl 1):S7-13.

Luong A, Marple BF. Sinus surgery: indications and techniques. Clin Rev Allergy Immunol 2006;30:217-22.

Abdi-Ali A, Mohammadi-Mehr M, Agha Alaei Y. Bactericidal activity of various antibiotics against biofilm-producing *Pseudomonas aeruginosa*. Int J Antimicrob Agents 2206;27:196-200.

Jefferson KK, Goldmann DA, Pier GB. Use of confocal microscopy to analyze the rate of vancomycin penetration through *Staphylococcus aureus* biofilms. Antimicrob Agents Chemother 2005;49:2467-73.

Walters MC 3rd, Roe F, Bugnicourt A, Franklin MJ, Stewart PS. Contributions of antibiotic penetration, oxygen limitation, and low metabolic activity to tolerance of *Pseudomonas aeruginosa* biofilms to ciprofloxacin and tobramycin. Antimicrob Agents Chemother 2003;47:317-23.

Palmer JN. Bacterial biofilms: do they play a role in chronic sinusitis? Otolaryngol Clin N Am 2005;38:1193-1201.

Donlan RM. Biofilms: microbial life on surfaces. Emerg Infect Dis 2002;8:881-90.

Potera C. Forging a link between biofilms and disease. Science 1999;283:1837, 1839.

Post JC, Stoodley P, Hall-Stoodley L, Ehrlich GD. The role of biofilms in otolaryngologic infections. Curr Opin Otolaryngol Head Neck Surg 2004;12:185-90.

Tonnaer EL, Graamans K, Sanders EA, Curfs JH. Advances in understanding the pathogenesis of pneumococcal otitis media. Pediatr Infect Dis J 2006;25:546-52.

Rayner MG, Zhang Y, Gorry MC, Chen Y, Post CJ, Ehrlich GD. Evidence of bacterial metabolic activity in culture-negative otitis media with effusion. JAMA 1998;279:296-9.

Dingman JR, Rayner MG, Mishra S, Zhang Y, Ehrlich MD, Post JC, et al. Correlation between presence of viable bacteria and presence of endotoxin in middle-ear effusions. J Clin Microbiol 1998;36:3417-9.

Perloff JR, Palmer JN. Evidence of bacterial biofilms in a rabbit model of sinusitis. Am J Rhinol 2005;19:1-9.

Chiu A, Antunes M, Feldman M, Cohen N. Dose-dependent effects of topical tobramycin in an animal model of *Pseudomonas* sinusitis. In: Programs and abstracts of the 52nd Annual Meeting of the American Rhinologic Society; Sep. 16, 2006; Toronto, ON, Canada.

Witterick IJ, Kolenda J. Surgical management of chronic rhinosinusitis. Immunol Allergy Clin N Am 2004;24:119-34.

Lieu JE, Piccirillo JF. Methodologic assessment of studies on endoscopic sinus surgery. Arch Otolaryngol Head Neck Surg 2003;129:1230-5.

Lavigne F, Tulic MK, Gagnon J, Hamid Q. Selective irrigation of the sinuses in the management of chronic rhinosinusitis refractory to medical therapy: a promising start. J Otolaryngol 2004;33:10-16.

"Protein Polymer Technologies Product Research" dated Mar. 28, 2006, 2 pages, downloaded from the Internet Archive at: http://web.archive.org/web/20060328113942/www.ppti.com/Market/Research.html.

Gross, Charles W., et al., "Autologus Fibrin Sealant Reduces Pain After Tonsillectomy", The Laryngoscope 111, pp. 259-263 (Feb. 2001).

Kitajiri et al., "Relief of Post-Tonsillectomy Pain by Release of Lidocaine From Fibrin Glue", The Laryngoscope 111, pp. 642-644 (Apr. 2001).

Vaiman Michael et al., "Fibrin Sealant Reduces Pain After Tonsillectomy: Prospective Randomized Study", Annals of Otology, Rhinology & Laryngology 115 (7), pp. 483-489 (2006).

Archer, Sanford M. MD, *Nasal Polyps, Nonsurgical Treatment*, eMedicine, dated Oct. 19, 2004, downloaded from the Internet Archive at: http://web.archive.org/web/20041019082359/http://www.emedicine.com/ent/topic334.htm.

Atridox®, Package insert and Carton Label Rev 7 (Feb. 2003).

Kumar et al., "Inhibition of Inflammation and Roflumilast and Dexamethasone in Murine Chronic Asthma", Journal of Pharmacology and Experimental Therapeutics, vol. 307, No. 1, pp. 349-355 (2003).

CollaGenex Atridox® web page, dated Sep. 26, 2004, downloaded from the Internet Archive at: http://web.archive.org/web/20041205004132/collagenex.com/pr_atridox.asp.

Lechapt-Zalcman et al., *Increased expression of matrix metalloproteinase-9 in nasal polyps*, Journal of Pathology, 193:233-241 (2001).

Kyung, Lee S. et al., *Doxycycline reduces airway inflammation and hyperresponsiveness in a murine model of toluene diisocyanate-induced asthma*, Journal of Allergy and Clinical Immunology [online] (May 2004).

Watelet, J.B. et al., *Matrix metalloproteinases MMP-7, MMP-9 and their tissue inhibitor TIMP-1: expression in chronic sinusitis vs. nasal polyposis*, Allergy, 59:54-60 (2004).

Plateltex, "Reduce fibrosis-Reducing scarring-Autologous Platelets", accessed on Jan. 26, 2010 from: http://www.plateltex.com/lp_reduce_fibrosis.html.

Stoeckli, Sandro J. et al., "A Prospective Randomized Double-Blind Trial of Fibrin Glue for Pain and Bleeding After Tonsillectomy", Laryngoscope 109: pp. 652-655, (Apr. 1999).

Granick Mark MD et al., "Toward a common language: surgical wound bed preparation and debridement", Wound Repair and Regeneration, 14, S1-S10, © the Wound Healing Society, (2006).

Stetter, Christopher et al., "Skin grafting of a chronic leg ulcer with combined Versajet™—V.A.C. therapy", XP-002566870 Case Reports, JDDG, 4:739-742 (2006).

Nagoba, B.S. et al., A Simple and Effective Approach for the Treatment of Chronic Wound Infections Caused by Multiple Antibiotic Resistant *Escherichia coli*, Journal of Hospital Infection, 69:177-180 (2008).

Banin, Ehud et al., "Chelator-Induced Dispersal and Killing of *Pseudomonas aeruginosa* Cells in a Biofilm", Applied and Environmental Microbiology, vol. 72, No. 3, pp. 2064-2069 (Mar. 2006).

Chang, D.M., the Binding of Free Calcium Ions in Aqueous Solution Using Chelating Agents, Phosphates and Poly (Acrylic Acid), JAOCS, vol. 60, No. 3, pp. 618-622 (Mar. 1983).

"Medicine Encyclopedia" M., RLS, p. 561( 2001)—Miramistin solution 0.01%.

Yamada et al., "Chitosan Based Water-Resistant Adhesive. Analogy to Mussel Glue", *Biomacromolecules* 2000, 1 (2), pp. 252-258 (Apr. 13, 2000).

* cited by examiner

SOLVATING SYSTEM AND SEALANT FOR MEDICAL USE IN THE SINUSES AND NASAL PASSAGES

CROSS REFERENCE TO RELATED APPLICATION

This application is a continuation-in-part of copending U.S. patent application Ser. No. 11/431,495 filed May 10, 2006, the entire disclosure of which is incorporated herein by reference.

FIELD OF THE INVENTION

This invention relates to the treatment of chronic rhinosinusitis and other bacterial sinus conditions.

BACKGROUND

Chronic rhinosinusitis (CRS) is inflammation of the paranasal sinuses and is associated with anterior or posterior nasal discharge, nasal obstruction or facial pressure, pain or fullness lasting for at least about twelve weeks. CRS affects an estimated 10% or more of the U.S. population. Most patients with CRS are initially treated with medical therapy, but hundreds of thousands undergo functional endoscopic sinus surgery (FESS) for refractory CRS every year. Patients with CRS often have a reduced quality of life, and may require billions of dollars in annual health-care and lost work time costs. CRS is a Th1 and Th2 inflammatory response to a number of mechanisms including but not limited to bacterial toxins, extracellular polysaccharide matrices secreted by bacteria and contained within a bacterial biofilm, fungi, developed allergic reactions to both bacteria and fungi (IgE) and auto immune disorders. Bacteria associated with CRS and its accompanying inflammation include *Staphylococcus aureus, Pseudomonas aeruginosa, Streptococcus pneumonia, Haemophilus influenzae* and *Moraxella catarrhalis*. Biofilms containing one or more of these species and possibly also containing fungi may be a factor in the pathogenesis of CRS, see e.g., Ramadan et al., "Chronic rhinosinusitis and biofilms", Otolaryngol Head Neck Surg. 132:414-417 (2005) and Ferguson et al., "Demonstration of Biofilm in Human Bacterial Chronic Rhinosinusitis", Am J Rhinol, 5:19, pp. 452-57 (2005). Biofilms form when bacteria interact with a surface to form polymeric films (sometimes referred to as exopolysaccharide or extracellular polysaccharide polymers) that coat the surface and provide a living colony for further bacterial proliferation. Bacteria lodged in biofilms are much more difficult to remove or kill than bacteria in a plaktonic (suspended) state, and are extremely resistant to many antibiotics and biocides. The extracellular polysaccharide (EPS) matrix, the toxins produced by the bacterial colony, and the fungi that the bacterial biofilm may harbor may each be capable of inciting an inflammatory response from the host.

SUMMARY OF THE INVENTION

Although antibiotics may initially be administered at elevated dosages to address CRS, they are generally ineffective as they cannot penetrate the bacterial cell walls through the EPS and cannot interrupt cell division as bacteria at the core of a bacterial biofilm are sessile and not dividing. Additionally, antibiotic administration can promote drug resistance in the targeted and other bacterial species. It would be highly desirable to employ alternative treatments that permit a reduction or elimination in the amount of required antibiotics yet discourage recurrence of the treated condition. When the treated condition involves a bacterial biofilm on a tissue surface, it would be desirable to remove or disrupt the biofilm so that remaining bacteria may more effectively be attacked by antibiotics or by the body's own natural defenses. It would also be desirable to at least temporarily seal or otherwise protect the thus-treated surface in order to repel bacterial adherence and biofilm reformation. It would also be desirable to do so while meeting biocompatibility requirements for contact with human tissue, and while using small dosages of administered materials and short periods of application.

The present invention provides in one aspect a method for treating rhinosinusitis and other bacterial sinus conditions, which method comprises:

a) applying a solvating system comprising a surfactant to a treatment site comprising a bacterial biofilm attached or adhered to a surface within a nasal or sinus cavity, b) detaching, removing or otherwise disrupting at least a part of the biofilm, and c) applying to the treatment site a protective layer of a polymeric film-forming medical sealant.

The invention provides in another aspect a composition for discouraging bacterial recolonization and biofilm reformation on tissue from which a biofilm has been removed, the composition comprising a polymeric film-forming medical sealant and an antimicrobial agent comprising a gallium-containing compound.

The disclosed method may be used for rhinological treatment or post-operative care, and may be used to treat maladies or chronic conditions including chronic rhinosinusitis and other bacterial sinus conditions.

BRIEF DESCRIPTION OF THE DRAWING

Like reference symbols in the various figures of the drawing indicate like elements. The elements in the drawing are not to scale.

DETAILED DESCRIPTION OF THE PREFERRED EMBODIMENTS

Figure 1:
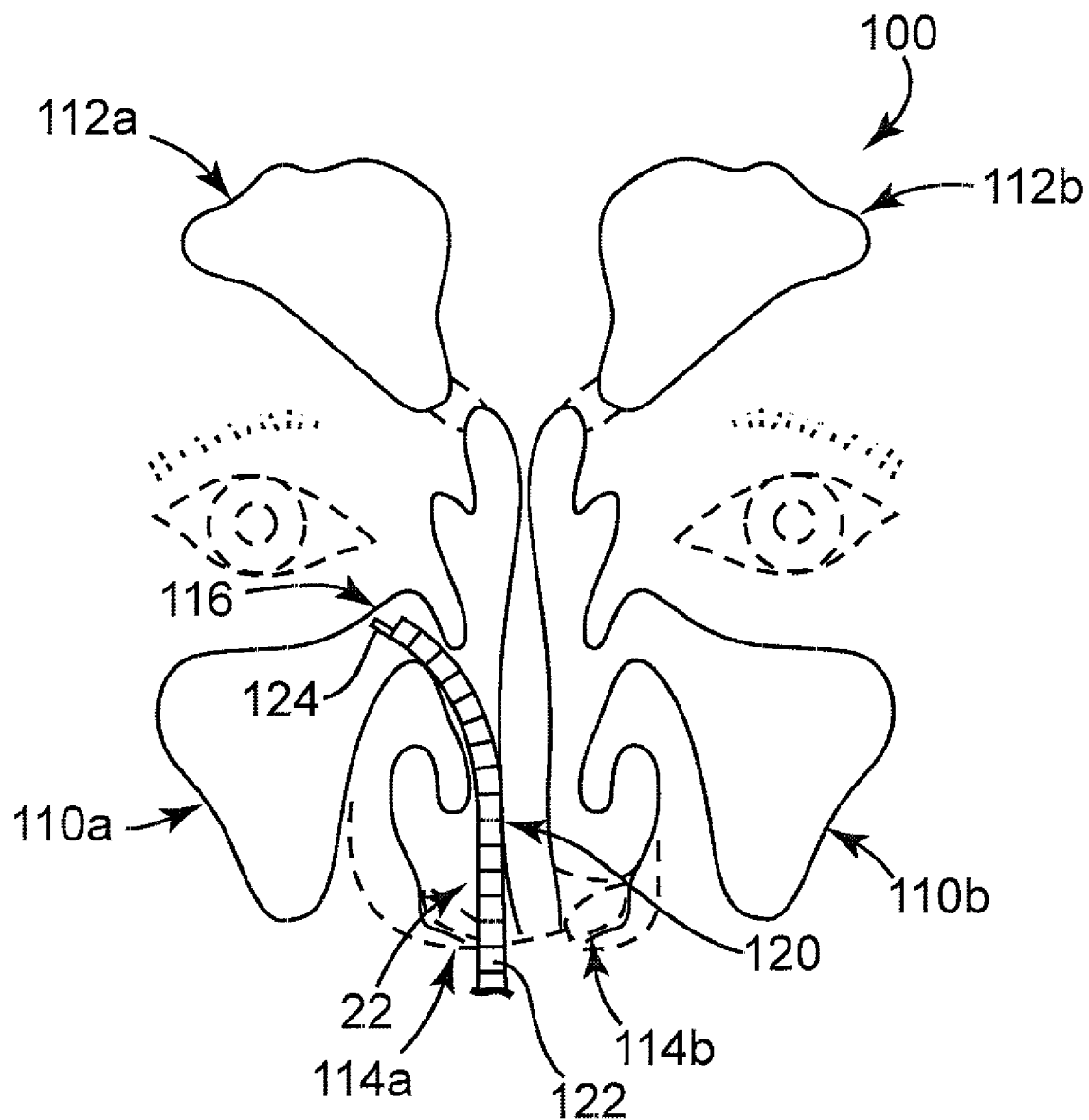
FIG. 1 is a schematic view showing the disclosed method.

The following detailed description describes certain embodiments and is not to be taken in a limiting sense. All weights, amounts and ratios herein are by weight, unless otherwise specifically noted. The terms shown below have the following meanings:

The term "antimicrobial agent" refers to a substance having the ability to cause greater than a 90% numeric reduction (viz., at least a 1-log order reduction) in a population of one or more of *Staphylococcus aureus, Pseudomonas aeruginosa, S. pneumonia, Haemophilus influenzae* or *Moraxella catarrhalis* or any other bacteria implicated in the etiology of chronic rhinosinusitis using the bacterial plate count procedure described below in the Examples.

The terms "attached" and "adhered" when used in reference to a bacterial biofilm and a surface mean that the biofilm is established on and at least partially coats or covers the surface, and has some resistance to removal from the surface. As the nature of this relationship is complex and poorly understood, no particular mechanism of attachment or adherence is intended by such usage.

The term "adhesion" refers to the sticking together of a material to tissues or tissue to tissue with which it is in intimate contact for extended periods or tissue that connects opposing tissues or prosthetic materials across a normally open space.

The term "bacterial biofilm" means a community of bacteria attached to a surface, with the organisms in the community being contained within an EPS matrix produced by the bacteria.

The term "biocompatible" when used in reference to a substance means that the substance presents no significant deleterious or untoward effects upon the body.

The term "biodegradable" when used in reference to a substance means that the substance will degrade or erode in vivo to form smaller chemical species. Such degradation process may be enzymatic, chemical or physical.

The term "bioresorbable" when used in reference to a substance means that the substance is capable of being absorbed by the body.

The terms "detaching", "removing" and "disrupting" when used in reference to a bacterial biofilm attached or adhered to a surface mean that at least a significant amount of the biofilm initially present on the surface no longer is attached or adhered to the surface. No particular mechanism of detachment, removal or disruption is intended by such usage.

The term "hemostat" means a device or material which stops blood flow.

The term "nasal or sinus cavities" refers to the various tissues defining the normally air-filled passages and chambers within the nose and sinus including but not limited to the nostrils or nares, the nasal concha or turbinates, the frontal, ethmoid, sphenoid and maxillary sinuses, the sinus ostia and the nasopharnyx, and to objects or articles (e.g., prostheses, packing or stents) that may be placed within a nasal or sinus cavity.

The term "polymeric sealant" means that the sealant is either formed from a synthetic crosslinked or uncrosslinked polymer or is a natural material such as a protein which has been crosslinked (e.g., synthetically crosslinked).

The term "residence time" when used in reference to a polymeric sealant at a treatment site means the time period during which the sealant remains in place in vivo under gross observation.

The term "sequestering agent" means a chemical that will combine with another material, especially a metal ion, to discourage or prevent the material from coming out of solution. The term "metal ion sequestering agent" means a sequestering agent that will combine with one or more metal ions such as alkali metals, alkaline earth metals, iron and the like to discourage or prevent the metal ion from coming out of solution. In order of increasing atomic number the alkali metals are lithium, sodium, potassium, rubidium, cesium, and francium, and the alkaline earth metals are beryllium, magnesium, calcium, strontium, barium, and radium.

The term "solvating" means to form a solution or dispersion containing a solvent or other carrier within which a solute is dissolved or suspended.

Referring to FIG. 1, the disclosed method may be performed in the nasal or sinus cavities 100 of a patient, including the maxillary sinuses 110a, 110b and frontal sinuses 112a, 112b, which may be accessed through nares 114a, 114b. It should be noted that external features of the patient, including nares 114a, 114b, are shown in dashed lines. When the patient suffers for example from chronic rhinosinusitis, one or more treatment sites such as treatment site 116 associated with a surface of maxillary sinus 110a may be surgically addressed to substantially remove part or all of the biofilm at the treatment site and prevent or discourage bacterial recolonization. Treatment site 116 includes ciliated epithelium of maxillary sinus 110a and an associated layer of bacteria inhabiting an associated biofilm (not shown in FIG. 1). The treatment site need not be natural tissue and may instead be an artificial structure (not shown in FIG. 1) such as a sinus packing or stent covered at least in part with a layer of bacterial biofilm. The disclosed solvating system may be applied treatment site 116 using an introducer 120 with an articulatable nozzle 122 containing an irrigation duct (hidden in FIG. 1) through which the solvating system may flow to the distal end of introducer and thence to the treatment site. The solvating system and residues of the biofilm may be removed from the treatment site via an aspiration duct (hidden in FIG. 1). The disclosed polymeric film-forming medial sealant may likewise be applied at the treatment site using the same or a different irrigation duct in introducer 120. Those skilled in the art will appreciate that the solvating system, sealant or both solvating system and sealant may be applied to the treatment site using other methods or devices. Exemplary other methods include trephination and exemplary other devices include syringes (e.g., glass syringes and bulb syringes).

Figure 2:
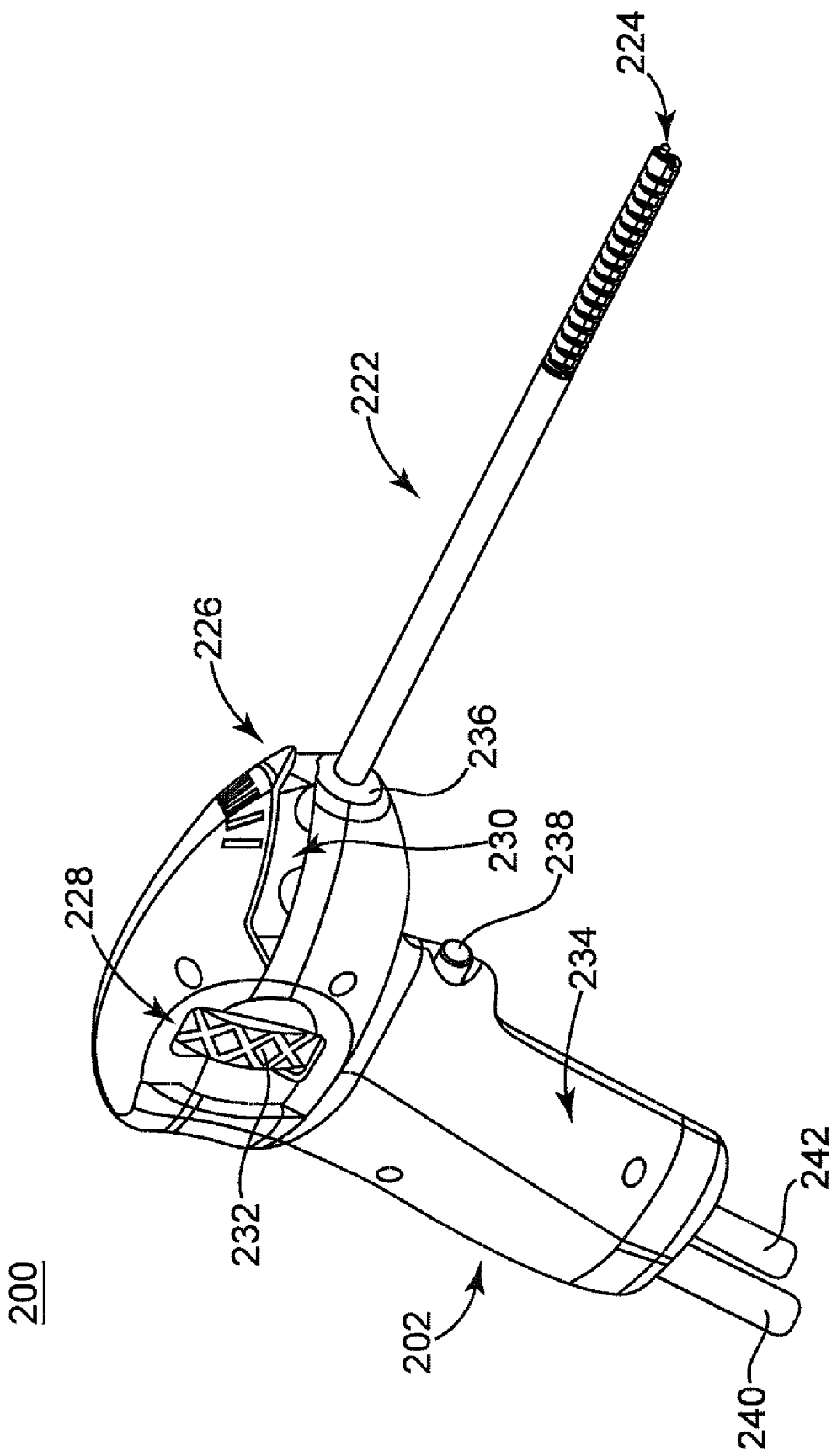
FIG. 2 is a perspective view of a surgical biofilm removal instrument which may be used in the disclosed method.

FIG. 2 shows an exemplary biofilm removal surgical instrument 200 which may be used in the disclosed method. Instrument 200 includes a handle 202, an introducer 222, a nozzle 224 (referenced generally) and irrigation and aspiration ducts (not shown in FIG. 2). Instrument 200 can optionally further include a first actuator assembly 226 (referenced generally) and a second actuator assembly 228 (referenced generally). A control wheel 230 in first actuator assembly 226 may be operable by a user to effectuate bending of the introducer 222, and a control wheel 232 in second actuator assembly 228 may be operable by a user to effectuate movement or rotation of nozzle 224 relative to introducer 222. The handle 202 serves generally as a housing for various other components of instrument 200 and retains introducer 222. Handle 202 may have a pistol grip-like shape, defining a grip portion 234 and a nose 236. The grip portion 234 is sized and shaped for grasping by a user's hand, whereas the nose 236 is adapted for connection to the introducer 222. Trigger 238 and an associated sensor and valve (not shown in FIG. 2) may be used to control the flow of the disclosed solvating system through irrigation tubing 240 and thence to the distal end of introducer 222 through nozzle 224 and onto the desired treatment site. Trigger 238 may be provided with a multidirectional range of motion and associated with one or more additional sensors and valves (not shown in FIG. 2) to control removal of the solvating system, biofilm residue and other debris from the treatment site through nozzle 224 and thence to aspiration tubing 242. Trigger 238 may also be used to control the flow of the disclosed sealant through a separate lumen in irrigation tubing 240 and thence to the distal end of introducer 222 through nozzle 224 and onto the desired treatment site.

The solvating system may be applied to the desired treatment site to detach, remove or otherwise disrupt at least a part of a bacterial biofilm attached or adhered to at least a portion of the nasal or sinus cavities. The solvating system desirably is applied in at least an amount and thickness sufficient to cover the desired portion of the biofilm. The treatment may involve chemical dilution or mechanical disruption. For example, the solvating system may be applied as a pressurized spray to dislodge the bacterial biofilm, bacteria and other foreign body buildup at the treatment site. Application of the solvating system or other liquids (e.g., saline solution) may be performed using pressure, spray patterns, motion or other techniques to accomplish hydrodebridement at the treatment site. While not wishing to be bound by theory, the solvating system may dissolve the biofilm and bring it into solution or suspension so that the thus-disrupted biofilm can be easily flushed or otherwise removed from the treatment site using aspiration, lavage or other removal techniques. Any remaining bacteria at the treatment site may then more readily be attacked by an antimicrobial agent or by the body's natural defenses. Bacterial attack may for example be assisted by including an antimicrobial agent in the solvating system or in the polymeric film-forming medical sealant, or by separately applying an antimicrobial agent intra operatively or post operatively (e.g., topically, orally or systemically). It may be desirable to inject sufficient solvating system into the treatment area to displace any pus or other material that may be present, allowing excess material to overflow from the treatment area until the color of the excess material no longer changes. The solvating system may be left in place until it can drain away or is otherwise eliminated or resorbed, or the solvating system may be allowed to stand for a suitable time (e.g., a few minutes, a few hours or longer) and then may be rinsed away using saline or another suitable liquid. Application of the solvating system and removal of dislodged or disrupted biofilm and bacteria may also be repeated as desired to ensure thorough removal of the offending organisms.

To discourage bacterial recolonization and biofilm reformation, the polymeric film-forming medical sealant is also applied to the treatment site. This may for example be accomplished using an introducer 120 or 222 as shown in FIG. 1 and FIG. 2 to dispense the film-forming medical sealant onto the treatment site. The applied sealant may fill the treated nasal or sinus cavities or may be applied as a film or other conformal coating that leaves at least a partial air opening in the treated cavities. The sealant desirably adheres to natural tissues at the treatment site and resists detachment or other disruption until natural degradation or resorption of the sealant takes place (e.g., after a residence time of one or more days or weeks). Meanwhile recolonization or reinfection may be significantly reduced or prevented, and improved healing and reciliation may take place. The sealant may provide various therapeutic advantages including but not limited to bacterial adhesion repellence, anti-infective properties, local immune modulation, tissue protection, reduction or elimination of pain or bleeding, reduction in inflammation, optimization of environment for ciliary regrowth, reduction in adhesions to critical anatomy, or the like. These advantages may arise due to a variety of mechanisms including a) inhibiting bacterial colonization, b) inhibiting the adherence of bacteria to tissue, c) reducing tissue morbidity or abscess formation, d) reducing or preventing disease recurrence (for example, specifically reducing the chronic inflammation related to bacterial toxin and EPS), e) coating and protecting tissue during healing, such as by maintenance of a moist wound which promotes platelet aggregation, or by closure of a dry wound without excessive scabrous formation, f) hemostasis, g) optimizing the environment for reciliation of the mucosa, h) speeding the growth or regrowth of cilia and i) delivering therapeutic agent(s) to the treatment site. Desirably the sealant will attach to a portion of the mucosa, cover other portions of the mucosa while leaving the cilia in such unattached portions free to undergo natural rhythmic cilia motion (viz., cilia beating), deliver antimicrobial agents or additional therapeutic agents as needed, and prevent bacteria from adhering to the treatment site.

A variety of solvating systems may be used in the disclosed method. As noted above, the solvating system comprises surfactant. The surfactant desirably is water-soluble and non-toxic. Exemplary surfactants include anionic surfactants, nonionic surfactants, cationic surfactants and zwitterionic surfactants. Exemplary anionic surfactants include but are not limited to $C_6$-$C_{24}$ alkylbenzene sulfonates; $C_6$-$C_{24}$ olefin sulfonates; $C_6$-$C_{24}$ paraffin sulfonates; cumene sulfonate; xylene sulfonate; $C_6$-$C_{24}$ alkyl naphthalene sulfonates; $C_6$-$C_{24}$ alkyl or dialkyl diphenyl ether sulfonates or disulfonates, $C_4$-$C_{24}$ mono or dialkyl sulfosuccinates; sulfonated or sulfated fatty acids; $C_6$-$C_{24}$ alcohol sulfates (for example $C_6$-$C_{12}$ alcohol sulfates); $C_6$-$C_{24}$ alcohol ether sulfates having 1 to about 20 ethylene oxide groups; $C_4$-$C_{24}$ alkyl, aryl or alkaryl phosphate esters or their alkoxylated analogues having 1 to about 40 ethylene, propylene or butylene oxide units; and mixtures thereof. For example, the anionic surfactant may be sodium chenodeoxycholate, N-lauroylsarcosine sodium salt, lithium dodecyl sulfate, 1-octanesulfonic acid sodium salt, sodium cholate hydrate, sodium deoxycholate, sodium dodecyl sulfate (also known as sodium lauryl sulfate) or sodium glycodeoxycholate.

Exemplary cationic surfactants include but are not limited to quaternary amine compounds having the formula:

where R, R', R" and R'" are each a $C_1$-$C_{24}$ alkyl, aryl or aralkyl group that can optionally contain one or more P, O, S or N heteroatoms, and X is F, Cl, Br, I or an alkyl sulfate. For example, the cationic surfactant may be hexadecylpyridinium chloride monohydrate or hexadecyltrimethylammonium bromide.

Exemplary nonionic surfactants include but are not limited to $C_6$-$C_{24}$ alcohol ethoxylates (for example $C_6$-$C_{14}$ alcohol ethoxylates) having 1 to about 20 ethylene oxide groups (for example about 9 to about 20 ethylene oxide groups); $C_6$-$C_{24}$ alkylphenol ethoxylates (for example $C_8$-$C_{10}$ alkylphenol ethoxylates) having 1 to about 100 ethylene oxide groups (for example about 12 to about 20 ethylene oxide groups); $C_6$-$C_{24}$ alkylpolyglycosides (for example $C_6$-$C_{20}$ alkylpolyglycosides) having 1 to about 20 glycoside groups (for example about 9 to about 20 glycoside groups); $C_6$-$C_{24}$ fatty acid ester ethoxylates, propoxylates or glycerides; $C4$-$C_{24}$ mono or di alkanolamides; and mixtures thereof. For example, the nonionic surfactant may be polyoxyethyleneglycol dodecyl ether, N-decanoyl-N-methylglucamine, digitonin, n-dodecyl B-D-maltoside, octyl B-D-glucopyranoside, octylphenol ethoxylate, polyoxyethylene (8) isooctyl phenyl ether, polyoxyethylene sorbitan monolaurate or polyoxyethylene (20) sorbitan monooleate.

Exemplary zwitterionic surfactants include but are not limited to aminoalkylsulfonate compounds having the formula:

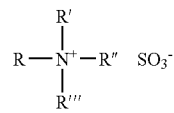

where R, R', R" and R'" are each a $C_1$-$C_{24}$ alkyl, aryl or aralkyl group that can optionally contain one or more P, O, S or N heteroatoms; amine oxide compounds having the formula:

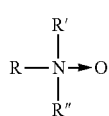

where R, R'and R" are each a $C_1$-$C_{24}$ alkyl, aryl or aralkyl group that can optionally contain one or more P, O, S or N heteroatoms; and betaine compounds having the formula:

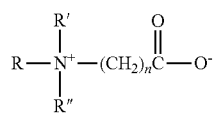

where R, R'and R" are each a $C_1$-$C_{24}$ alkyl, aryl or aralkyl group that can optionally contain one or more P, O, S or N heteroatoms, and n is about 1 to about 10. For example, the zwitterionic surfactant may be 3-[(3-cholamidopropyl)dimethylammonio]-2-hydroxy-1-propane sulfonate, 3-[(3-cholamidopropyl)dimethylammonio]-1-propane sulfonate (sometimes referred to as CHAPS), 3-(decyldimethylammonio)propanesulfonate inner salt (sometimes referred to as caprylyl sulfobetaine), or N-dodecyl-N,N-dimethyl-3-ammonio-1-propanesulfonate.

Preferred surfactants include alkyl sulfates, alkyl sulfonates, aryl sulfonates and zwitterionic surfactants. The desired surfactants may be obtained as pure compounds or in some instances may be obtained by using products such as liquid Castile soap. The surfactant may for example be present at a concentration of at least about 0.002 M, at least about 0.005 M or at least about 0.01 M, e.g., about 0.002 to about 1 M, about 0.005 to about 0.7 M or about 0.01 to about 0.5 M. Expressed on a weight basis, the surfactant may for example be greater than about 0.2 wt. % of the solvating system, e.g., about 0.3% to about 30%, about 0.5% to about 25% or about 1% to about 20% of the solvating system. Increased surfactant amounts may promote faster biofilm breakup.

The solvating system may optionally contain a metal ion sequestering agent. The sequestering agent desirably is a mild acid whose acidity is sufficient to sequester one or more metal ions in the exopolysaccharide or extracellular polysaccharide matrix, but which is not so acidic so as to harm the treated nasal or sinus cavity tissue. Metal ions of particular interest (due to their likely involvement in the targeted bacterial biofilms) include sodium, calcium and iron. The metal ion sequestering agent desirably is water-soluble and nontoxic. Representative acids include but are not limited to carboxylic acids, diacids, or triacids such as formic acid, acetic acid, chloroacetic acid, dichloroacetic acid, oxalic acid, oxamic acid, glycolic acid, lactic acid, pyruvic acid, aspartic acid, fumaric acid, maleic acid, succinic acid, iminodiacetic acid, glutaric acid, 2-ketoglutaric acid, glutamic acid, adipic acid, citric acid, glucuronic acid, mucic acid, nitrilotriacetic acid, salicylic acid, ketopimelic acid, benzoic acid, mandelic acid, chloromandelic acid, phenylacetic acid, phthalic acid and boric acid; mineral acids such as hydrochloric acid, orthophosphoric acid and phosphonic acid; and mixtures thereof. Citric acid is a preferred acid. The metal ion sequestering agent may for example be present at a concentration of at least about 0.01 M, at least about 0.05 M or at least about 0.1 M, e.g., about 0.01 to about 0.5 M, about 0.05 to about 0.4 M or about 0.1 to about 0.3 M. Increased metal ion sequestering agent amounts may promote faster biofilm breakup.

The solvating system may optionally include a variety of other ingredients, including water and other solvents (e.g., alcohols), buffering agents, antimicrobial agents and a variety of adjuvants. Preferably the solvating system contains water and one or more buffering agents. The buffering agent preferably maintains the solvating system at an appropriate pH for contacting human tissue, and desirably at a pH greater than 5. For example, the solvating system may be buffered to have a near-neutral pH, e.g., a pH greater than 5 and less than 8.5. Buffering agents may for example be up to about 25% of the solvating system. Exemplary buffering agents include but are not limited to potassium chloride, glycine, potassium hydrogen phthalate, sodium acetate, potassium hydrogen phthalate, barbitone sodium and sodium citrate. When the metal ion sequestering agent is a mild acid, the buffering agent desirably is a salt of that acid.

Solvating systems containing one or more antimicrobial agents are also preferred. The EPS matrix allows the biofilm to stick to an underlying surface and also protects the embedded organisms; thus, bacteria in biofilms are approximately 100 to 1000 times more resistant to the effects of antibiotics than planktonic bacteria. After the biofilm has been broken down into unbound polymers or fragments and solvated or otherwise disrupted by the solvating system, an antimicrobial agent can much more effectively attack the remaining bacteria. Exemplary antimicrobial agents include active oxygen compounds such as hydrogen peroxide, isolated or equilibrium derived or isolated peracids such as chloroperbenzoic acids, peracetic acid, perheptanoic acid, peroctanoic acid, perdecanoic acid, performic acid, percitric acid, perglycolic acid, perlactic acid, perbenzoic acid, and monoester peracids derived from diacids or diesters such as adipic, succinic, glutaric, or malonic acid; amphenicols; ampicillins; ansamycins; beta-lactams such as carbacephems, carbapenems, cephalosporins, cephamycins, monobactams, oxacephems, penicillins and any of their derivatives; carboxylic esters such as p-hydroxy alkyl benzoates and alkyl cinnamates; chitosan salts; cubic-phase lipids; gallium-containing antimicrobial agents such as gallium acetylacetonate, gallium bromide, gallium chloride, gallium fluoride, gallium iodide, gallium maltolate, gallium nitrate, gallium nitride, gallium percolate, gallium phosphide and gallium sulfate; iodo-compounds and other active halogen compounds such as iodine, interhalides, polyhalides, metal hypochlorites, hypochlorous acid, metal hypobromites, hypobromous acid, chloro- and bromo-hydantoins, chlorine dioxide and sodium chlorite; lincosamides; macrolides; nitrofurans; organic peroxides including benzoyl peroxide and alkyl benzoyl peroxides; ozone; phenolic derivatives including o-phenyl phenol, o-benzyl-p-chlorophenol, tert-amyl phenol and $C_1$-$C_6$ alkyl hydroxy benzoates; quaternary ammonium compounds such as alkyldimethylbenzyl ammonium chloride and dialkyldimethyl ammonium chloride; quinolines; singlet oxygen generators; sulfonamides; sulfones; sulfonic acids such as dodecylbenzene sulfonic acid; tetracyclines; vancomycin; derivatives thereof and mixtures thereof. Many of these recited agents represent classes containing useful specific materials whose individual utility will be recognized by persons having ordinary skill in the art. For example, exemplary penicillins include but are not limited to amdinocillin, amdinocillin pivoxil, amoxicillin ampicillin, apalcillin, aspoxicillin, axidocillin, azlocillin, acampicillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G. procaine, penicillin N, penicillin O, penicillin V, penicillin V banzathine, penicillin V hydrabamine, penimepicycline, phenethicillin potassium, piperacillin, pivampicillin propicillin, quinacillin, sulbenicillin, sultamicillin, talampicillin, temocillin, ticarcillin and mixtures thereof or with other materials (e.g., penicillins combined with clavulanic aid such as the combination of amoxicillin and clavulanic acid available as AUGMENTIN™ from GlaxoSmithKline).

An antimicrobial agent such as those described above may optionally be applied in a separate treatment step (if need be in a suitable carrier) after application of the solvating system and before application of the polymeric film-forming medical sealant. An antimicrobial agent may also be applied as a part of the sealant. Whether applied as a part of the solvating system, in a separate step, or as a part of the sealant, the antimicrobial agent preferably provides greater than a 99% numeric reduction (viz., at least a 2-log order reduction), greater than a 99.9% numeric reduction (viz., at least a 3-log order reduction), greater than a 99.99% numeric reduction (viz., at least a 4-log order reduction) or greater than a 99.999% numeric reduction (viz., at least a 5-log order reduction) in a population of one or more of *S. aureus, P. aeruginosa, S. pneumonia, H. influenzae* or *M. catarrhalis* bacteria using the bacterial plate count procedure described below in the Examples.

The solvating system may contain additional therapeutic agents. Exemplary therapeutic agents include any material suitable for rhinologic use including analgesics, anti-cholinergics, anti-fungal agents, antihistamines, steroidal or non-steroidal anti-inflammatory agents, anti-parasitic agents, antiviral agents, biostatic compositions, chemotherapeutic/antineoplastic agents, cytokines, decongestants, immunosuppressors, mucolytics, nucleic acids, peptides, proteins, steroids, vasoconstrictors, vitamins, mixtures thereof, and other therapeutic materials that will be apparent to those skilled in the art. Several such additional therapeutic agents are discussed in more detail below in connection with the polymeric film-forming medical sealant. Other adjuvants that may be included in the solvating system include dyes, pigments or other colorants (e.g., FD & C Red No. 3, FD & C Red No. 20, FD & C Yellow No. 6, FD & C Blue No. 2, D & C Green No. 5, D & C Orange No. 4, D & C Red No. 8, caramel, titanium dioxide, fruit or vegetable colorants such as beet powder or beta-carotene, turmeric, paprika and other materials that will be familiar to those skilled in the art); indicators; flavoring or sweetening agents including but not limited to anise oil, cherry, cinnamon oil, citrus oil (e.g., lemon, lime or orange oil), cocoa, eucalyptus, herbal aromatics (e.g., clove oil, sage oil or cassia oil), lactose, maltose, menthol, peppermint oil, saccharine, sodium cyclamate, spearmint oil, sorbitol, sucrose, vanillin, wintergreen oil, xylitol and mixtures thereof; antioxidants; antifoam agents; and rheology modifiers including thickeners and thixotropes.

The solvating system desirably has a sufficiently low viscosity to enable easy delivery to the treatment site using for example power spray or other spray application, lavage, misting, mopping, wicking or dripping. The solvating system desirably also may be easily removed from the treatment site by subsequent flushing, rinsing, draining or absorption. The solvating system need not be applied in liquid form and may for example be applied as a powder, gel, foam, sponge, film strip or other suitable form. The solvating system desirably does not contain ingredients which might potentially harm tissues or structures in the nasal or sinus cavities.

A variety of polymeric film-forming medical sealants may be used in the disclosed method. The sealant preferably is a biodegradable or bioresorbable material having a residence time in vivo of from one day to a few (e.g., 2, 3 or 4) days, weeks or months. The sealant may be uncrosslinked, crosslinked before being applied to the treatment site, or crosslinked after application. In one embodiment, the sealant may be a viscoelastic material. In another embodiment, the sealant may harden after application. The sealant may be a synthetic polymer (for example, polyethylene glycol or PEG), natural polymer (for example, a polysaccharide, lipid or polypeptide), or a synthetically-modified natural polymer (for example, a polypeptide reacted with PEG). Other exemplary synthetic polymers include polyacetals, polyacrylic acid, polyalkylene oxalates, polyalkylene succinates, polyamides, polyamino acids, polyaspartic acid, polyanhydrides, polycaprolactones, polycarbonates, polycyanoacrylates, polydiaxonones, polyesteramides, polyetheresters, polyethylene oxide (PEO), poly(glycolic acids) and other poly(glycolides), polyhydroxybutyrates, polyhydroxyvalerates, polyketals, poly(lactic acid) and other polylactides including poly(lactide-co-glycolides), poly(malic acids), polyorthoesters, polyphosphazines, polyphosphoesters, polypropylene oxide (PPO), degradable polyurethanes, polyvinyl alcohol (PVA), polyvinyl pyrrolidone (PVP), and copolymers, terpolymers, blends, and mixtures thereof.

Exemplary polysaccharides include cellulose and its derivatives such as oxidized cellulose, hydroxyethyl cellulose, carboxymethyl cellulose (CMC), carboxymethyl amylose (CMA), carboxyethyl cellulose and hydroxypropylmethyl cellulose (HPMC); chitin; chitosan and its derivatives such as carboxymethyl chitosan and trimethylchitosan; dextran and its derivatives such as carboxymethyl dextran; glycogen; glycosaminoglycans such as hyaluronan (e.g., hyaluronic acid and its derivatives including esters and polymers), heparin, heparin sulfate, dermatin sulfate, and chondroitin-6-sulfate; gums such as alginate, gellan gum and xanthan gum; pectin; and starch and its derivatives.

Exemplary lipids include glyceryl based lipid compounds such as glyceryl monooleate, and liquid crystal lipids which can be delivered in fluid form and which when in contact with moisture will convert to a cubic phase to provide a waxy cubic or crystalline material.

Exemplary polypeptides include albumin, collagen, gelatin, silk and their derivatives. For example, crosslinked hydrogels may be formed from many polypeptides by reacting them with a suitable crosslinking agent such as an aldehyde (e.g., glutaraldehyde or formaldehyde), carbodiimide, chitin, CMC or a glycol such as a PEG.

The polymeric film-forming medical sealant may include antimicrobial agents, additional therapeutic agents and other adjuvants like those mentioned above in connection with the solvating system. Sealants containing therapeutic agents that offer both anti-infective and anti-inflammatory properties (e.g., tetracyclines) are a preferred embodiment. Sealants containing additional therapeutic agents such as anti-fungal agents, antihistamines, steroidal or non-steroidal anti-inflammatory agents, anti-parasitic agents, antiviral agents, chemotherapeutic/antineoplastic agents, decongestants or mucolytics are another preferred embodiment. Sealants containing antimicrobial agents and additional therapeutic agents are yet another preferred embodiment. Exemplary anti-fungal agents include but are not limited to allylamines, imidazoles, polyenes, thiocarbamates, triazoles, derivatives thereof and mixtures thereof. Exemplary antihistamines include but are not limited to azelastine, diphenhydramine, loratidine, derivatives thereof and mixtures thereof. Exemplary steroidal anti-inflammatory agents include but are not limited to 21-acetoxypregnenolone, alclometasone, algestone, amcinonide, beclomethasone, betamethasone, budesonide, chloroprednisone, clobetasol, clobetansone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethosone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, derivatives thereof and mixtures thereof. Preferred steroidal anti-inflammatory agents include beclomethasone, budesonide, fluticasone proprionate and mometasonefuroate. Exemplary nonsteroidal anti-inflammatory agents include but are not limited to COX inhibitors (COX-1 or COX nonspecific inhibitors) and selective COX-2 inhibitors. Exemplary COX inhibitors include but are not limited to salicylic acid derivatives such as aspirin, sodium salicylate, choline magnesium trisalicylate, salicylate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam); alkanones such as nabumetone; derivatives thereof and mixtures thereof. Exemplary COX-2 inhibitors include but are not limited to diaryl-substituted furanones such as refecoxib; diaryl-substituted pyrazoles such as celecoxib; indole acetic acids such as etodolac and sulfonanilides such as nimesulide; derivatives thereof and mixtures thereof. Exemplary anti-parasitic agents include but are not limited to atovaquone clindamycin, dapsone, iodoquinol, metronidazle, pentamidine, primaquine, pyrimethamine, sulfadiazine, trimethoprim/sufamethoxazole, trimetrexate, derivatives thereof and mixtures thereof. Exemplary antiviral agents include but are not limited to acyclovir, famciclovir, valacyclovir, edoxudine, ganciclovir, foscamet, cidovir (available as VISTIDE™ from Gilead Sciences, Inc.), vitrasert, formivirsen, HPMPA (9-(3-hydroxy-2-phosphonomethoxypropyl)adenine), PMEA (9-(2-phosphonomethoxyethyl)adenine), HPMPG (9-(3-hydroxy-2-(phosphonomethoxy)propyl)guanine), PMEG (9-[2-(phosphonomethoxy)ethyl]guanine), HPMPC (1-(2-phosphonomethoxy-3-hydroxypropyl)-cytosine), ribavirin, EICAR (5-ethynl-1-beta-D-ribofuranosylimidazole-4-carbonxamine), pyrazofurin (3-[beta-D-ribofuranosyl]-4-hydroxypyrazole-5-carboxamine), 3-Deazaguanine, GR-92938X (1-beta-D-ribofuranosylpyrazole-3,4-dicarboxamide), LY253963 (1,3,4-thiadiazol-2-yl-cyanamide), RD3-0028 (1,4-dihydro-2,3-benzodithiin), CL387626 (4,4'-bis[4,6-di][3-aminophenyl-N,N-bis(2-carbamoylethyl)-sulfonilimino]-1,3,5-triazine-2-ylamino-biphenyl-2-,2'-disulfonic acid disodium salt), BABIM (bis[5-amidino-2-benzimidazoly-1]-methane), NIH351, derivatives thereof and mixtures thereof. Exemplary chemotherapeutic/antineoplastic agents include but are not limited to antitumor agents (e.g., cancer chemotherapeutic agents, biological response modifiers, vascularization inhibitors, hormone receptor blocks, and cryotherapeutic agents or other agents that destroy or inhibit neoplasia or tumorigenesis) such as alkylating agents or other agents which directly kill cancer cells by attacking their DNA (e.g., cyclophosphamide and isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU)), antitumor antibiotics and other compounds that act by binding or intercalating DNA and preventing RNA synthesis (e.g., doxorubicin, daunorubicin, epirubicin, idarubicin, mitomycin-C and bleomycin), plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, triazole inhibitors such as letrozole and anastrazole, and steroidal inhibitors such as exemastane), antiangiogenic proteins, small molecules, gene therapies or other agents that inhibit angiogenesis or vascularization of tumors (e.g., meth-1, meth-2 and thalidomide), bevacizumab (available as AVASTIN™ from Genentech), squalamine, endostatin, angiostatin, ANGIOZYME™ from Ribozyme Pharmaceuticals, neovastat (available as AE-941™ from Aeterna Zentaris), CC-5013 (available as REVIMID™ from Celgene Corp.), medi-522 (available as VITAXIN™ from MedImmune, Inc.), 2-methoxyestradiol or 2ME2 (available as PANZEM™ from Entremed, Inc.), carboxyamidotriazole (CAI), combretastatin A4 prodrug (CA4P), SU6668, SU11248, BMS-275291, COL-3, EMD 121974, IMC-1C11, IM862, TNP-470, celecoxib (available as CELEBREX™ from Pfizer Inc.), refecoxib, interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, bacillus calmette-guerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, chlorambucil, cytarabine, dacarbazine, etoposide, flucarbazine, flurouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine streptocin, taxol or paclitaxel, taxotere, analogs/congeners, derivatives thereof and mixtures thereof. Exemplary decongestants include but are not limited to epinephrine, oxymetazoline, phenylephrine, pseudoephedrine, tetrahydrozolidine, xylometazoline, derivatives thereof and mixtures thereof. Exemplary mucolytics include but are not limited to acetylcysteine, dornase alpha, guaifenesin, derivatives thereof and mixtures thereof.

In those instances where it is desirable to remove water from tissue, e.g., to remove fluid from polyps or edematous tissue, a hyperosmolar agent may be employed in the sealant. Exemplary hyperosmolar agents include but are not limited to furosemide, sodium chloride gel and other salt preparations that draw water from tissue or substances that directly or indirectly change the osmolar content of the mucous layer. Where sustained release or delayed release of the therapeutic agent is desirable, a release agent modifier may also be included in the sealant.

The sealant desirably has a sufficiently low viscosity to enable easy delivery to the treatment site using for example power spray or other spray application, lavage, misting, mopping, wicking or dripping. The sealant need not be applied in liquid form and may for example be applied as a powder, gel, foam, sponge, film strip or other suitable form. The applied sealant may be bioresorbable or biodegradable after a desired period of time once healing has occurred. The sealant desirably includes at least one characteristic that promotes retention of the sealant at the treatment site. This characteristic may be selected from a variety of features including but not limited to thickness, size, shape, density, viscosity, hardness, bioadhesiveness, mucoadhesiveness, manner of application or insertion, and the like. The sealant may prevent bacterial recolonization or the formation or reformation of bacterial biofilms by covering the treatment site (e.g., mucosa from which a bacterial biofilm has been removed by the solvating system) with an alternative film structure whose surface is not readily penetrable by bacteria associated with bacterial sinus conditions. The sealant desirably does not contain ingredients which might potentially harm tissues or structures in the nasal or sinus cavities.

The solvating system and sealant may desirably be used as a part of a multi-step treatment regimen which disrupts the bacterial biofilm and discourages its return. For example, a series of steps that may be broadly classified as Cleansing/Disrupting, Killing, Protecting/Coating, Aerating, and Healing may be carried out. The Cleansing/Disrupting step may be carried out by administering the solvating system as described above. The Killing step may be carried out by applying a suitable antimicrobial agent to the treatment site. This may as described above be accomplished by including an antimicrobial agent in the solvating system, in the sealant, or in both the solvating system and sealant. As noted above, an antimicrobial agent may also be applied as a separate step between application of the solvating system and application of the sealant. An antimicrobial agent may also be applied or administered post operatively. The Protecting/Coating step may be carried out by coating at least part of the thus-treated tissue with a protective sealant layer as described above. The Aerating step may be carried out by providing air passageways or improving air passageways to the treated tissues by opening occluded or partially occluded nasal passages, sinuses or sinus ostia. This may for example be accomplished by surgically removing obstructive tissue structures or by manually displacing such structures. The Healing step may be carried out by allowing the cleansed, protected and sealed tissue surface to undergo a return to a normal state, e.g., through one or more healing mechanisms such as modulation of an inflammatory response, phagocytosis, mucosal remodeling, reciliation or full or partial restoration of normal sinus function. The disclosed method may advantageously be accomplished without requiring surgery, for example by applying and removing the solvating system and by applying the sealant through normal aspiration/suction techniques or by simple flushing of affected nasal passages without infusing the solvating system or sealing into the more difficult to reach sinuses beyond the sinus ostia.

A comparable series of steps may be performed in a multi-step treatment regimen which disrupts a bacterial biofilm in a portion of the middle or inner ear. Further details regarding such a regimen may be found in copending application Serial No. (attorney docket no. 151-P-28168US01), filed even date herewith, the entire disclosure of which is incorporated herein by reference.

The invention is further illustrated in the following non-limiting examples.

EXAMPLE 1

Bacterial isolates of *S. aureus* and *P. aeruginosa* were recovered from the sinuses of patients with sinus disorders. Patients with cystic fibrosis or an underlying immunosuppressive disease (HIV infection, insulin-dependent diabetes mellitus, or renal disease) and patients who had taken antibiotics or oral prednisone in the previous month were excluded. All patients had refractory sinusitis, that is, persistent symptoms resistant to medical therapy despite having undergone technically successful functional endoscopic sinus surgery (FESS) for refractory chronic rhinosinusitis (CRS) with or without nasal polyposis. The occurrence of CRS was diagnosed in accordance with the 2003 American Academy of Otolaryngology—Head and Neck Surgery (AAO-HNS) guidelines set out in Benninger et al., "Adult chronic rhinosinusitis: Definitions, diagnosis, epidemiology, and pathophysiology", Otolaryngol Head Neck Surg 129 (3 suppl):S1-S32 (2003). The selected patients had been refractory to medical therapy for more than 12 months before sample collection, and the failure of FESS was judged not to be associated with technical factors such as obstructive synechiae, frontal sinus obstruction, or a retained uncinate process. Samples were collected consecutively until 10 specimens each of *S. aureus* and *P. aeruginosa* were obtained using direct endoscopic guidance and the procedure described by Nadel et al., "Endoscopically guided cultures in chronic sinusitis", Am J Rhinol 12:233-241 (1998). Briefly, a topical anesthetic agent was administered, the nasal ala retracted, and an endoscope used to visualize the middle meatus and sinus cavities. A thin, flexible calcium alginate swab (STARSWAB II™ Collection and Transport System, Starplex Scientific, Etobicoke, Ontario) was inserted and directed to the site with the most purulence. If no purulence was observed, the surface of the maxillary sinus was swabbed for 15 seconds. Care was taken to avoid contact with the lateral nasal wall or nasal vestibule. Samples were plated and incubated using standard procedures. Bacteria were identified using a VITEK 2™ system (Biomérieux, Durham, N.C.). Crystal violet staining to confirm the presence of biofilms was performed according to the method described by Stepanovic et al., "A modified microtiter-plate test for quantification of staphylococcal biofilm formation", J Microbiol Methods 40:175-179 (2000). For incubation and culture, previously frozen strains were inoculated on trypticase soy agar (TSA) with 0.5% sheep blood. After 24 hours, one to four colonies per strain were cultured on TSA. Cultures were incubated at 37° C. for 24 hours to condition them to a trypticase soy broth (TSB)-TSA medium and ensure noncontamination. Colonies grown on TSA solid medium were then amplified in 5 mL of TSB medium with 0.5% glucose according to the method described by Gotz, "*Staphylococcus* and biofilms", Mol Microbiol 43:1367-1378 (2002) and incubated at 37° C. for at least 24 hours.

A drip-flow reactor (DFR) was used to determine the effectiveness of various test solutions delivered to *S aureus* and *P aeruginosa* biofilms on hydroxyapatite (HA)-coated microscope slides for removing these bacterial biofilms with and without hydrodynamic force. The slides in the DFR are tipped at 10° from the horizontal, thereby modeling a low shear environment. The DFR was housed in an incubator at 37° C. under aerobic conditions. Approximately 20 minutes before bacterial inoculation, sterile medium (10% TSB for *S aureus*; 1% TSB for *P aeruginosa*) was dripped on the slides in the DFR and allowed to collect over the slides to form a conditioning layer. The slides were then inoculated with 1 mL of a culture of either *S aureus* or *P aeruginosa*. The DFR was tilted so that the slides would be horizontal for 4 hours to allow bacterial attachment to the substrate. Subsequently, the DFR was set so that the slides were once again at a 10° angle, with sterile medium dripping on the slides at a rate of 10 mL per hour. After 3 days, biofilm-removal experiments were performed. Two methods were used to treat the biofilms formed by each bacterial species. The first application method involved a static treatment in the DFR, with a solvating agent (referred to as CAZS) being dripped onto the biofilms. The CAZS solvating agent contained deionized water, 25 g/L (corresponding to 0.13 M) citric acid, 5.35 g/L (corresponding to 0.02 M) caprylyl sulfobetaine zwitterionic surfactant ($CH_3(CH_2)_9N^+(CH_3)_2CH_2CH_2CH_2SO_3^-$, CAS 15163-36-7) and sufficient sodium citrate (about 240 g/L) to buffer the system to pH 5.4. The second application method involved delivery of saline or delivery of CAZS outside the DFR, using a pressurized jet lavage to apply a hydrodynamic shearing force to the biofilm. For all treatments, preliminary runs were done to ensure that variations among slides were within acceptable limits. In addition, multiple plates of both bacterial species were produced to determine the within-run and run-to-run variations. A control slide was made for each DFR run. Three runs were evaluated for each treatment of each type of bacteria.

For static treatment, flow to the DFR was halted, the DFR was placed in a horizontal position, and the cover was removed. A 25 mL portion of CAZS was applied to one slide. Control slides were not treated with CAZS. After 10 minutes, the slides were rinsed with saline (25 mL). The DFR was then disconnected from the inflow tube, and each slide was removed under a laminar flow hood and placed in a sterile 50-mL tube. After another saline rinse (2 mL), the surface of the slide was scraped repeatedly, and the scrapings and saline were collected in the tube. The tube was vortexed for 10 seconds, sonicated for 2 minutes, and vortexed again for 10 seconds to disperse the bacteria into suspension. The suspensions were then serially diluted and 100-µL aliquots applied to three plates containing TSA and incubated at 37° C. for 24 hours. Colony-forming units (CFUs) were counted manually, and the number of CFUs per square centimeter was calculated. The resulting plate counts were log (10) transformed and expressed as the mean (±SD) value derived from plate counts from two DFR runs of three slides each.

For hydrodynamic treatment, the slides were removed from the DFR and placed in a glove box. The slides were placed in a holder and sprayed for approximately 20 seconds with about 150 mL of either saline or CAZS using a device that provided pressurized jet lavage. The spraying was done with both a side-to-side and an up-and-down sweeping motion so that all areas were sprayed twice, once in each axis. The slides were then placed in sterile 50-mL tubes, rinsed, scraped, dispersed, incubated and evaluated as described above.

The mean (±SD) percent reduction from control values in the quantity of S. aureus and P. aeruginosa bacteria (viz., the number of CFUs on each plate) after each treatment was calculated and the results assessed using two-sample t tests (MINITAB™ version 14, Minitab, State College, Pa.). A P value less than 0.05 was considered to represent a significant difference from the control value. The results are shown below in Table 1, expressed as the mean (±SD) number of colony-forming units per centimeter (log) derived from three plates assessed twice:

TABLE 1

Bacterial Plate Log Counts According to Type of Treatment

| Treatment | Staphylococcus aureus | Pseudomonas aeruginosa |
|---|---|---|
| None (Control) | 8.7 ± 0.4 | 9.2 ± 0.2 |
| Static CAZS delivery | 6.2 ± 0.3 | 6.3 ± 1.3 |
| Hydrodynamic saline delivery | 6.4 ± 0.2 | 6.9 ± 0.1 |
| Hydrodynamic CAZS delivery | 4.8 ± 0.3 | 4.0 ± 0.5 |

The results in Table 1 show that significant bacterial biofilm removal was obtained. Before treatment, ample biofilms formed in the DFR cultures of both S. aureus and P. aeruginosa, with CFU counts for these Controls ranging from 7.8 to 9.5 log/cm$^2$. Static administration of CAZS resulted in a 2.5 log reduction ($5.11 \times 10^8$ to $1.65 \times 10^6$; P=0.001) in the number of S. aureus CFUs and a 2.9 log reduction ($1.69 \times 10^9$ to $1.91 \times 10^6$; P=0.002) in the number of P. aeruginosa CFUs. Mechanical disruption using hydrodynamic saline delivery alone decreased the number of S. aureus CFUs by 2.3 log units ($5.11 \times 10^8$ to $2.38 \times 10^6$; P=0.001) and the number of P. aeruginosa CFUs by 2.4 log units ($1.69 \times 10^9$ to $7.31 \times 10^6$; P=0.001). However, mechanical disruption using hydrodynamic CAZS decreased the S. aureus CFU count by 3.9 log units ($5.11 \times 10^8$ to $6.37 \times 10^4$; P=0.001) and the P. aeruginosa CFU count by 5.2 log units ($1.69 \times 10^9$ to $1.04 \times 10^4$; P=0.001).

Confocal scanning laser microscopy (CSLM) was performed on three slides (for each treatment and bacteria species) not subjected to plate counts to allow imaging of the biofilm architecture in control and treated samples. The slides were stained for CSLM using a BACLIGHT™ Live/Dead kit (Molecular Probes, Invitrogen, Carlsbad, Calif.) containing two nucleic acid stains (SYTO 9, which detects living cells by fluorescing green, and propidium iodide, which detects dead cells by fluorescing red). After staining, the slides were examined using CSLM at a 630× magnification using a LEICA™ SP2 acoustic-optical beam splitter with a 2-photon MAI TAI™ attachment (Leica Microsystems, Bannockburn, Ill.) and fluorescence excitation and detection in both the green and red spectra. Each slide area was divided into 10 equally sized segments. A microscopic field was selected at random from each segment, and images were obtained at 1-µm intervals from the top of the biofilm to the substrate, thereby creating an image stack for each location. The CSLM analysis revealed that a thick biofilm carpeted the Control slides. Hydrodynamic treatment with saline and static treatment with CAZS decreased the amount of biofilm coverage markedly and reduced the organization of the remaining biofilm. Hydrodynamic treatment with CAZS produced a greater reduction both in biofilm coverage and in the amount of order in the biofilm community. The results corresponded generally to the plate count assessments with respect to the relative reductions in the amount of biofilm achieved with each treatment.

Of the three treatments investigated, power irrigation using CAZS and a pressurized jet lavage was the most effective in disrupting the bacterial biofilms. Power irrigation using saline had appreciable biofilm-reducing effects. However, the presence of a surfactant and citric acid in the irrigation solution significantly enhanced the reduction in CFU count in both S. aureus and P. aeruginosa biofilms. Large, statistically significant reductions occurred, with the mean decreases in bacterial plate counts being 3.9 and 5.2 log (a reduction of 10,000 to 100,000 times), respectively, for S. aureus and P. aeruginosa biofilms. A decrease of this magnitude in vitro indicates that an appropriate in vivo treatment in the nasal or sinus cavities should effectively disrupt bacterial biofilms found there. Any remaining low level of persistent bacterial infection might be dealt with by host defenses or a topically or orally administered antimicrobial agent, and by application of a sealant as described above.

EXAMPLE 2

Experimental work conducted using *S aureus* and *P aeruginosa* cultures grown on TSA solid medium (viz., cultures made without use of HA-coated glass slides and the DFR and less likely to include a durable biofilm) indicates that a solvating system containing the surfactant but no metal ion sequestering agent may be less effective as a biofilm disruptor than a solvating system which also contains the metal ion sequestering agent. However, either solvating system may be a more effective biofilm disrupter than saline solution.

EXAMPLE 3

The CAZS solvating system employed in Example 1 was modified by replacing some of the water with gallium nitrate so that the modified system contained 25% gallium nitrate. A Control solution containing 25% gallium nitrate in deionized water was also prepared. When evaluated using the static treatment technique of Example 1, administration of the gallium nitrate Control solution resulted in a 3.4 log reduction (average of 4 runs) in the number of *S. aureus* CFUs and a 4.1 log reduction (average of 3 runs) in the number of *P. aeruginosa* CFUs. Static administration of the solution containing CAZS and gallium nitrate resulted in a 5.2 log reduction (average of 2 runs) in the number of *S. aureus* CFUs and a 5.5 log reduction (average of 2 runs) in the number of *P. aeruginosa* CFUs.

Although specific embodiments have been illustrated and described herein for purposes of description of the preferred embodiments, it will be appreciated by those of ordinary skill in the art that a wide variety of alternate or equivalent implementations calculated to achieve the same purposes may be substituted for the specific embodiments shown and described without departing from the scope of the present invention. This application is intended to cover any adaptations or variations of the preferred embodiments discussed herein. Therefore, it is manifestly intended that this invention be limited only by the claims and the equivalents thereof.

We claim:

1. A method for treating rhinosinusitis and other bacterial sinus conditions, which method comprises:
    a) applying an aqueous solvating system comprising a metal ion sequestering agent and a surfactant to a treatment site comprising a bacterial biofilm comprising an extracellular polysaccharide matrix attached or adhered to a surface within a nasal or sinus cavity,
    b) detaching, removing or otherwise disrupting at least a part of the biofilm by solvating the extracellular polysaccharide matrix so as to provide greater than a 1-log order reduction in one or more of *Staphylococcus aureus, Pseudomonas aeruginosa, S. pneumonia, Haemophilus influenzae* or *Moraxella catarrhalis* bacteria, and then
    c) applying to the treatment site a protective layer of a polymeric film-forming sealant.

2. A method according to claim 1 wherein the treatment site is in a nasal cavity.

3. A method according to claim 1 wherein the treatment site is in a sinus cavity.

4. A method according to claim 1 comprising applying the solvating system by spraying, lavage, misting, mopping, wicking or dripping and further comprising removing the solvating system from the treatment site by flushing, rinsing, draining or absorption after applying the solvating system and before applying the sealant.

5. A method according to claim 1 comprising applying the sealant by spraying, lavage, misting, mopping, wicking or dripping.

6. A method according to claim 1 comprising applying the sealant as a conformal coating.

7. A method according to claim 1 wherein the surfactant comprises a cationic surfactant.

8. A method according to claim 1 wherein the surfactant comprises a zwitterionic surfactant.

9. A method according to claim 1 wherein the surfactant is at least 0.2% of the solvating system.

10. A method according to claim 1 wherein the surfactant is about 0.3% to about 30% of the solvating system.

11. A method according to claim 1 wherein the surfactant is about 0.5% to about 25% of the solvating system.

12. A method according to claim 1 wherein the metal ion sequestering agent comprises a sequestering agent for sodium, calcium or iron.

13. A method according to claim 1 wherein the metal ion sequestering agent comprises citric acid.

14. A method according to claim 1 wherein the metal ion sequestering agent is present at a concentration of about 0.01 to about 0.5 M.

15. A method according to claim 1 wherein the solvating system has a pH of about 5 to about 8.5.

16. A method according to claim 15 wherein the solvating system further comprises a buffer.

17. A method according to claim 1 wherein the solvating system further comprises an antimicrobial agent.

18. A method according to claim 1 wherein the sealant is viscoelastic.

19. A method according to claim 1 wherein the sealant hardens after application.

20. A method according to claim 1 wherein the sealant comprises a polysaccharide.

21. A method according to claim 20 wherein the sealant comprises cellulose, chitin, chitosan, dextran, glycogen, glycosaminoglycan, gum, pectin, starch, or a derivative thereof.

22. A method according to claim 1 wherein the sealant comprises hyaluronan.

23. A method according to claim 1 wherein the sealant comprises carboxymethyl cellulose.

24. A method according to claim 1 wherein the sealant comprises a lipid or polypeptide.

25. A method according to claim 1 wherein the solvating system or sealant further comprises an antimicrobial agent.

26. A method according to claim 25 wherein the antimicrobial agent comprises gallium acetoacetonate, gallium bromide, gallium chloride, gallium fluoride, gallium iodide, gallium maltolate, gallium nitrate, gallium nitride, gallium percolate, gallium phosphite, gallium sulfate or mixture thereof.

27. A method according to claim 1 further comprising applying an antimicrobial agent after application of the solvating system and before application of the sealant.

28. A method according to claim 1 wherein the same steps performed in vitro will cause greater than a 1-log order reduction in a population of *Staphylococcus aureus*.

29. A method according to claim 1 wherein the same steps performed in vitro will cause greater than a 2-log order reduction in a population of one or more of *Staphylococcus aureus,*

*Pseudomonas aeruginosa, S. pneumonia, Haemophilus influenzae* or *Moraxella catarrhalis* bacteria.

30. A method according to claim 1 wherein the same steps performed in vitro will cause greater than a 3-log order reduction in a population of one or more of *Staphylococcus aureus, Pseudomonas aeruginosa, S. pneumonia, Haemophilus influenzae* or *Moraxella catarrhalis* bacteria.

31. A method according to claim 1 wherein the sealant further comprises an anti-fungal agent, antihistamine, steroidal or non-steroidal anti-inflammatory agent, anti-parasitic agent, antiviral agent, chemotherapeutic/antineoplastic agent, decongestant or mucolytic.

* * * * *